United States Patent
Bare et al.

[11] Patent Number: 5,806,515
[45] Date of Patent: Sep. 15, 1998

[54] SUPPLEMENTAL OXYGEN ADAPTER FOR TRACHEOSTOMY SPEAKING VALVES

[75] Inventors: Rex O. Bare, Lake Forest; Andrew J. Scherer, San Dimas, both of Calif.

[73] Assignee: Passy-Muir, Inc., Irvine, Calif.

[21] Appl. No.: 828,429

[22] Filed: Mar. 28, 1997

[51] Int. Cl.$^6$ .................................................. A61M 16/00
[52] U.S. Cl. ............................... 128/207.15; 128/207.14; 128/707.16; 623/9
[58] Field of Search ......................... 128/207.14, 207.15, 128/207.16, 207.29, 911; 623/9

[56] References Cited

U.S. PATENT DOCUMENTS

| | | | |
|---|---|---|---|
| 5,027,811 | 7/1991 | Tuxill | 128/207.14 |
| 5,515,844 | 5/1996 | Christopher | 128/207.29 |

FOREIGN PATENT DOCUMENTS

| | | | |
|---|---|---|---|
| 9014854 | 12/1990 | WIPO | 128/207.29 |

OTHER PUBLICATIONS

Shiley Phonate™ Speaking Valve with Oxygen Port, Product Designation: SSV SSVO by Mallinckrodt Medical, Inc.—Product Packaging (DP50–5209–002 (Jan. 1995)) and Instructions for Use Insert© Mallinckrodt Medical, Inc. 1994/DP50–5208–001 (Jan. 1995).

*Primary Examiner*—Mickey Yu
*Assistant Examiner*—V. Srivastava
*Attorney, Agent, or Firm*—Lyon & Lyon LLP

[57] ABSTRACT

An oxygen adapter for delivering low volume supplemental oxygen to a tracheostomized patient using a conventional tracheostomy speaking valve is provided, the adapter including a tube fitting for receiving conventional tubing thereon, and an outlet section attached to the tube fitting and defining a channel communicating between the tube fitting and an outlet end of the outlet section. The outlet section preferably extends axially from the tube fitting along the outer wall of a speaking valve to which the adapter is connected, the outlet end being located adjacent an inlet of the speaking valve, thereby delivering oxygen from the tubing received on the tube fitting to the inlet of the speaking valve. The adapter may be detachably connectable to the cylindrical wall of the speaking valve, preferably by a pair of semi-rigid gripping flanges adapted to peripherally engage the cylindrical wall of the speaking valve. The adapter preferably comprises injection-molded plastic, such as polycarbonate.

28 Claims, 3 Drawing Sheets

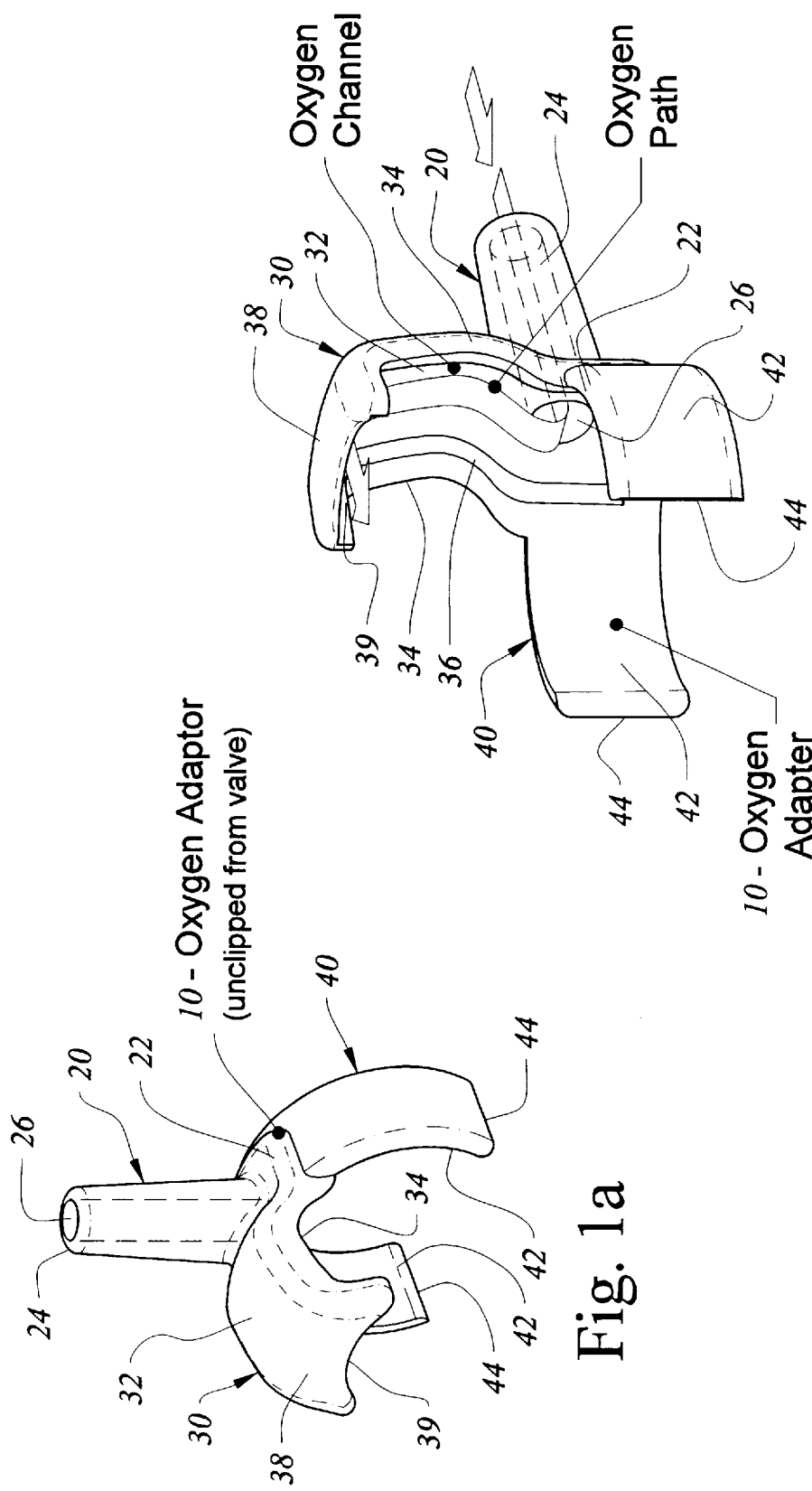

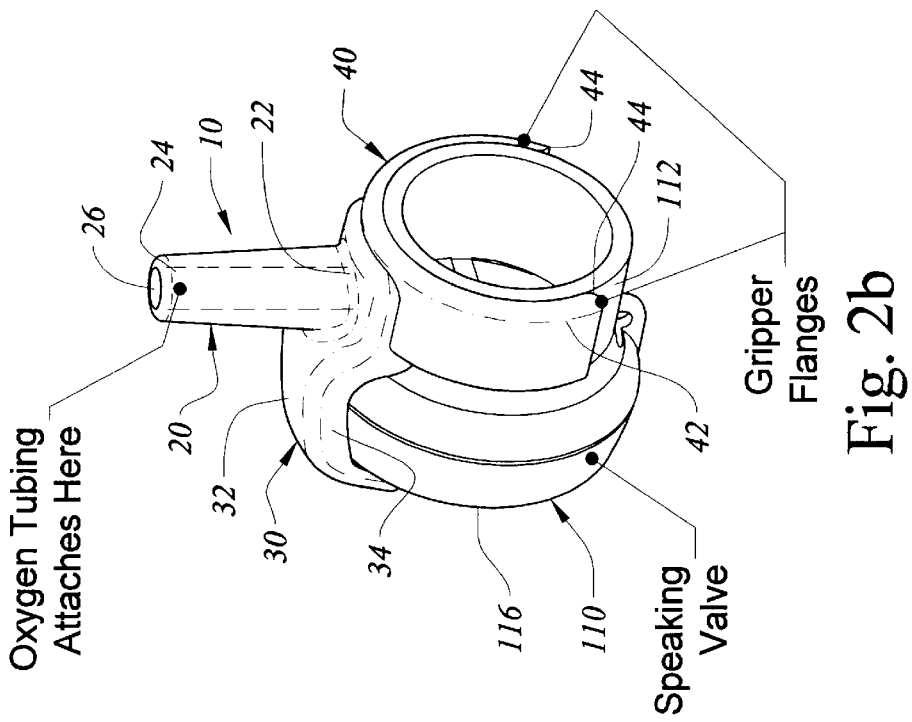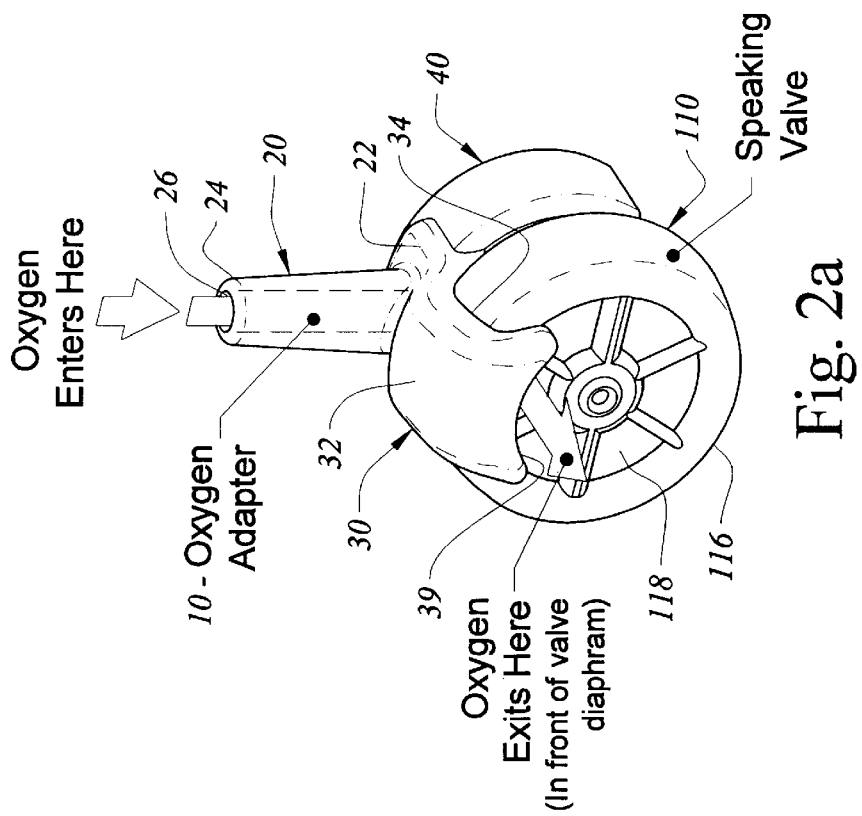

SUPPLEMENTAL OXYGEN ADAPTER FOR TRACHEOSTOMY SPEAKING VALVES

FIELD OF THE INVENTION

The present invention relates generally to speaking valves for tracheostomized patients, and more particularly to a device for connecting supplemental oxygen to a conventional tracheostomy speaking valve being used by a patient.

BACKGROUND

Tracheostomy tubes are often used to assist patients and other persons having respiratory problems, due to obstructions in their upper breathing passages or other medical conditions. A tracheostomy tube, generally comprising a small section of tubing, is typically introduced through an incision in the neck of the patient and into the trachea, generally below the larynx.

Once in place, an outer end of the tube generally extends from the patient's neck, preferably keeping a relatively low profile, and is fixed in place to prevent movement of the tube, typically by a neck plate attached to the tube that is fastened around the patient's neck by a strap. The outer end of the tube generally includes a hub or tapered fitting that facilitates connecting the patient to a ventilator or that can be left open to allow the patient to breathe freely through the tube.

One of the problems often experienced by tracheostomized patients is difficulty speaking because exhaled air generally exits out the tracheostomy tube and does not pass through their larynx. To remedy this, a speaking valve is often attached to the hub on the tube. The speaking valve generally comprises a hollow substantially cylindrical body, having a collar or taper on one end which facilitates attachment to the hub on the tube. The speaking valve includes a one-way check valve, generally a diaphragm mounted in the inlet of the valve, which opens to allow air flow into the speaking valve and the tracheostomy tube, but closes under positive back pressure, such as when a patient exhales. Thus, when the patient exhales, the speaking valve closes, causing air to travel up the trachea around the tracheostomy tube, through the larynx, and out the patient's nose and/or mouth, improving the patient's ability to speak.

In addition, tracheostomized patients often require supplemental oxygen, typically at relatively low flow rates of 6 liters per minute or less, which is generally delivered into the tracheostomy tube. When the patient has a speaking valve in place, this may require removing the speaking valve to attach oxygen tubing, causing substantial inconvenience removing and attaching the speaking valve. Alternatively, a hose or hood may be placed over the end of the speaking valve to deliver oxygen, but the weight and increased profile from such a device may increase stress on the tracheostomy tube and the patient.

Alternatively, a special speaking valve may be provided that has a tube fitting or side port integrally molded into the wall of the speaking valve. Tubing may be attached to the port, allowing oxygen to be provided into the tracheostomy tube without removing the speaking valve. Such a device generally includes a cap for closing the port when not in use, otherwise, air may escape out the port when the patient exhales, reducing the amount of air passing through the patient's larynx and making speech more difficult. The cap, generally a small loose fitting, is removed during oxygen delivery, potentially being dropped and/or misplaced by the patient or their caregiver. In addition, the small loose cap presents a particular risk to pediatric patients who may remove and possible try to ingest the cap.

One concern with such a device is that if the tubing is accidentally snagged, the speaking valve and/or tracheostomy tube may be pulled, possibly causing pain or distress to the patient and/or damage to the tracheostomy tube. In addition, the port is generally located between the diaphragm and the hub on the tracheostomy tube. Thus, pressurized oxygen is delivered through the port behind the one-way valve, which may cause pneumothorax, that is, undesired pressurization of the patient's lungs. In addition, the patient may experience other undesired effects, such as dryness in their throat and/or mucus build-up.

Therefore, there is a need for a device which provides improved delivery of supplemental oxygen to a tracheostomized patient using a speaking valve.

SUMMARY OF THE INVENTION

The present invention is directed to an adapter that is connectable to a conventional speaking valve and oxygen tubing, thereby allowing supplemental oxygen to be conveniently delivered to a tracheostomized patient using the speaking valve. In a preferred embodiment, the device is a single piece formed from injection-molded plastic, preferably a medical-grade polycarbonate, that may be detachably connected to a speaking valve.

Generally, the adapter comprises a tube fitting or port, a channel section, and a means for connecting the adapter to a speaking valve. The tube fitting has a base, an outer end, and a passage which extends between the outer end and the base. The outer end is generally shaped to receive tubing thereon, such as conventional tubing used to deliver low volume supplemental oxygen to tracheostomized patients. When the adapter is connected to a speaking valve, the base generally abuts the outer wall of the speaking valve, and the outer end extends away from the wall, preferably radially, although alternatively the outer end may extend diagonally or may be pivotally attached to the base.

The channel or outlet section is attached and preferably integrally molded to the tube fitting, and extends from the tube fitting, preferably substantially perpendicular thereto. The channel section includes a plurality of walls at least partially defining a channel which communicates with the passage in the tube fitting. Preferably, the channel section includes a top wall and two side walls, defining an inverted "U" cross-section.

When the adapter is connected to a speaking valve, the channel section extends axially along the outer wall of the speaking valve towards the inlet end thereof, preferably being contoured to substantially follow the shape of the outer wall of the speaking valve. The area of the outer wall under the channel section thereby preferably defines a fourth wall for the channel, allowing oxygen to travel through the channel without substantially leaking. Alternatively, the channel section may include a bottom wall that abuts and extends along the outer wall of the speaking valve. The bottom wall may comprises a thin film attached to the channel section, or it may comprise a wall integrally molded as part of the channel section of the adapter.

In addition, the channel section has an outlet end that generally extends to and/or over the inlet end of the speaking valve. Preferably, the outlet end defines a cowling that curves around the inlet end and is directed towards the inlet of the speaking valve, thus guiding oxygen exiting the channel towards the diaphragm of the speaking valve.

The adapter also generally includes mechanical means to connect the adapter to the speaking valve, preferably a pair of gripping flanges. The gripping flanges, which are attached and preferably integrally molded on either side of the base of the tube fitting, are curved and extend away from the tube fitting to define a partial annular shape. The inner surface of the gripping flanges thereby partially defines a substantially cylindrical shape, similar to that of the outer wall of the speaking valve. The gripping flanges generally comprise a resilient, semi-rigid material, such as injection-molded plastic, allowing the adapter to be connected to and disconnected from the speaking valve. Other means may also be used to detachably connect the adapter to a speaking valve, such as an adhesive patch or tape placed on the adapter, or straps, ties or other mechanical fasteners, engaging or attached to the adapter that may be wrapped around the speaking valve and fastened together. In addition, the adapter may be substantially permanently attached to the speaking valve using glue or other bonding materials.

To connect the adapter to a speaking valve, the adapter is generally oriented across the speaking valve with the gripping flanges straddling the outer wall of the speaking valve and the channel section directed axially towards the inlet end of the speaking valve. As the adapter is directed transversely onto the speaking valve, the ends of the gripping flanges contact the wall of the speaking valve, forcing the gripping flanges outward until they wrap peripherally around the speaking valve. The resilience of the gripping flanges causes their inner surface to substantially engage the wall of the speaking valve, thereby retaining the adapter on the speaking valve. After being used to deliver oxygen, the adapter is easily removed, simply by pulling it transversely away from the speaking valve, the semi-rigid gripping flanges resiliently disengaging from the outer wall of the speaking valve. Preferably the force required to attach and/or remove the adapter is sufficiently mild such that it does not cause pain, injury and/or damage to the tracheostomy tube or the patient.

The oxygen adapter of the present invention generally provides an improved device for delivering supplemental oxygen to a tracheostomized patient using a conventional speaking valve. Tubing, preferably conventional oxygen tubing, is attached to the outer end of the tube fitting, and the adapter is connected to a speaking valve as described above. Oxygen may then be delivered from a source connected to the tubing and through the adapter directly to the inlet of the speaking valve. Preferably, the gripping flanges engage the speaking valve such that the adapter may pivot around the valve to facilitate alignment with the oxygen supply tubing.

Alternatively, a speaking valve may be provided that includes an oxygen adapter as an integral part of, and preferably directly molded to, the speaking valve. The tube fitting may extend from the outer wall of the speaking valve, which may include a channel integrally formed in the outer wall communicating with the tube fitting. An integral cowling may then extend from the outlet of the channel extending around to the inlet end of the speaking valve to direct oxygen towards the inlet of the diaphragm.

When a patient using the adapter inhales, the diaphragm of the speaking valve opens to allow air in. Oxygen from the outlet end of the adapter is delivered in front of the diaphragm, allowing oxygen to freely enter into the speaking valve when the diaphragm is open. When the patient exhales, the diaphragm closes, preventing oxygen from entering the tracheostomy tube. Thus, the patient may exhale and/or speak with minimized risk of pneumothorax, dryness in the throat and other problems that may result from uninterrupted oxygen supply.

Accordingly, a principal object of the present invention is to provide an adapter for delivering supplemental oxygen to a tracheostomized patient who uses a conventional speaking valve.

It is also an object to provide an oxygen adapter that is easily connected to and removed from a conventional speaking valve.

It is also an object to provide a supplemental oxygen adapter that delivers oxygen to the inlet of a speaking valve, thereby allowing the tracheostomized patient to continue to use the speaking valve to ease speech during oxygen delivery.

Other objects and features of the present invention will become apparent from consideration of the following description taken in conjunction with the accompanying drawings.

BRIEF DESCRIPTION OF THE DRAWINGS

FIGS. 1a and 1b are perspective views of a preferred embodiment of an adapter in accordance with the present invention.

FIGS. 2a and 2b are perspective views of an adapter in accordance with the present invention connected to a conventional tracheostomy speaking valve.

DETAILED DESCRIPTION OF THE PREFERRED EMBODIMENTS

Figure 3:
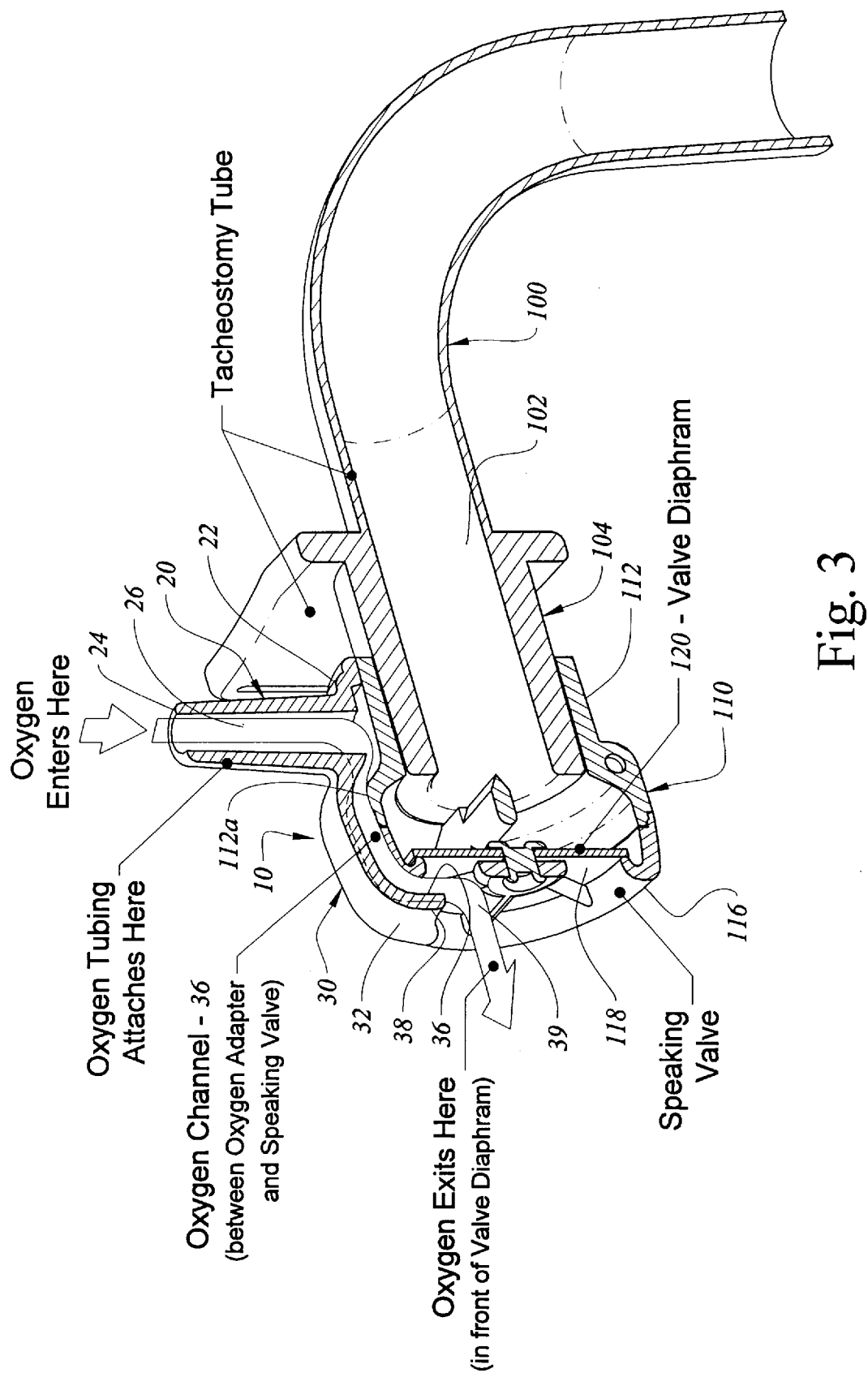
FIG. 3 is a cross-sectional view of an adapter in accordance with the present invention connected to a conventional speaking valve that is attached to a tracheostomy tube.

Turning now to the drawings, FIGS. 1a and 1b show a preferred embodiment of an adapter 10 for a tracheostomy speaking valve in accordance with the present invention. Generally, the adapter 10 comprises a tube fitting or port 20, a channel or outlet section 30, and a means for connecting the adapter 10 to a speaking valve 110 (see FIGS. 2a and 2b), such as the gripping flanges 40 shown in FIG. 1. The tube fitting 20 has a base 22, an outer end 24, and a passage 26 (shown in phantom) which extends through the tube fitting 20 between the outer end 24 and the base 22. The outer end 24 is generally shaped to receive tubing thereon (not shown), such as conventional tubing used to deliver low volume supplemental oxygen (generally 6 liters per minute and less) to a tracheostomized patient. As shown in FIG. 2b, the base 22 generally abuts the outer wall 112 of the speaking valve 110 when the adapter 10 is connected thereto, while the outer end 24 extends radially away from the outer wall 112.

Alternatively, the tube fitting 20 may extend diagonally or tangentially from the base or in some other direction other than radially from the base (not shown). In addition, the tube fitting 20 may be pivotally attached to the base 20, for example using a cooperating ball and socket joint (not shown). The base may include a rounded socket thereon into which a ball on the lower end of the tube fitting may be inserted. Such alternative embodiments may facilitate orientation of the tube fitting 20 to improve connection of the oxygen tubing.

The channel or outlet section 30 is attached to the tube fitting 20, preferably being integrally molded thereto, and preferably extends substantially perpendicularly from the tube fitting 20. As shown in FIG. 1a, the channel section 30 includes a plurality of walls at least partially defining a channel 36 which communicates with the passage 26 in the tube fitting 20. In the preferred embodiment, the channel section 30 includes a top wall 32 and two side walls 34, together defining an inverted "U" cross-section.

Referring again to FIGS. 2a and 2b, when the adapter 10 is connected to the speaking valve 110, the channel section 30 extends axially along the outer wall 112 of the speaking valve 110 towards the inlet end 116 thereof. The channel section 30 is contoured so that the top wall 32 generally follows the shape of the outer wall 112, thereby maintaining a substantially uniform cross-section for the channel 36, while the side walls 34 substantially engage and seal with the outer wall 112. Thus, as can be seen in FIG. 3, the area 112a of the outer wall 112 under the channel section 30 defines a fourth wall for the channel 36, allowing oxygen to travel through the channel 36 without leaking substantially. Alternatively, the channel section 30 may include a bottom wall (not shown) that abuts and extends along the area 112a of the wall 112. The bottom wall may comprise a thin film attached to the side walls 34 and the base 22 of the adapter, or it may comprise a wall integrally molded as part of the channel section 30 of the adapter 10.

In addition, the channel section 30 also includes an outlet end 38, generally extending to the inlet end 116 of the speaking valve 110. Preferably, the outlet end 38 is curved, thereby defining a cowling that extends around the inlet end 116 and directs the outlet 39 of the channel 36 towards the inlet 118 of the speaking valve 110. Oxygen exiting the outlet 39 of the channel 36 is thus delivered directly in front of the diaphragm 120 of the speaking valve 110, as shown in FIG. 2a.

The adapter 10 also generally includes mechanical means adapted to detachably connect the adapter 10 to the speaking valve 110, preferably a pair of gripping flanges 40, as shown in FIGS. 1a–2b. The gripping flanges 40 are attached on either side of the base 22 of the tube fitting 20, preferably being integrally molded thereto. The gripping flanges 40 are curved and extend away from the tube fitting 20 to define a partial annular shape, preferably something greater than half of an annulus. Thus, the inner surface 42 of the gripping flanges 40 partially defines a substantially cylindrical shape, similar to that of the outer wall 112 of the speaking valve 110. The material of the gripping flanges 40 is generally a resilient, semi-rigid material, such as injection-molded plastic, giving the gripping flanges 40 sufficient flexibility to move apart to allow the adapter 10 to be connected to the speaking valve 110, but resiliently returning to their original shape once connected to substantially engage the outer wall 112 of the speaking valve 110.

Other alternatives to mechanically connect the adapter 10 to the speaking valve 110 may also be used. For example, an adhesive patch or tape may be provided on the adapter 10, possibly attached to the bottom of the base 20, and/or on the outer wall 112 of the speaking valve 110. Alternatively, fasteners, such as straps or ties, may be wrapped around or integrally attached to the adapter 10, such as on opposite sides of the base 22 of the tube fitting 20. The fasteners may be wrapped around the speaking valve 110 and fastened together, possibly by tying them, or by locking cooperating tabbed and slotted ends, thereby substantially retaining the adapter 10 on the speaking valve. In addition, the adapter 10 may be substantially permanently attached to the speaking valve 110, for example using suitable conventional bonding materials.

The adapter 10 is preferably formed from injection-molded plastic, most preferably a medical-grade polycarbonate, such as that manufactured by Bayer Corporation of Pittsburgh, Pa. (Bayer model FCR 2458 Clear). The adapter may have multiple configurations, allowing it to be connectable to a variety of commercially available conventional speaking valves. In the preferred embodiment, the adapter is configured to connect to a low profile speaking valve for 15 mm tracheostomy tubes, such as the PMV 2000 manufactured by Passy-Muir, Inc. of Irvine, Calif.

To attach the adapter 10 to a conventional speaking valve 110, the adapter 10 is oriented with the gripping flanges 40 straddling the outer wall 112 and the channel section 30 extending axially towards the inlet end 116 of the speaking valve 110. As the adapter 10 is directed transversely onto the speaking valve 110, the ends 44 of the gripping flanges 40 contact the outer wall 112, forcing the gripping flanges 40 outward until the gripping flanges 40 wrap peripherally around the outer wall 112. The resilience of the gripping flanges 40 causes their inner surface 42 to substantially engage the outer wall 112 of the speaking valve 110. The friction between the inner surface 42 of the gripping flanges 42 and the outer wall 112 of the speaking valve and/or the resilience of the gripping flanges 40 thus retain the adapter 10 on the speaking valve 110. When no longer needed, the adapter 10 may be removed by pulling the adapter 10 transversely away from the speaking valve 110, forcing the gripping flanges 40 apart and disconnecting them from the outer wall 112 of the speaking valve 110.

The adapter 10 generally allows convenient delivery of a gas, such as supplemental oxygen, to a tracheostomized patient using a conventional speaking valve 110. The adapter 10 is connected to the speaking valve 110 which is attached to a tracheostomy tube 100 in a patient (not shown), as in FIG. 3. Tubing, such as conventional oxygen tubing (not shown), is attached to the outer end 24 of the tube fitting 20. Oxygen may then be delivered from a pressurized source connected to the tubing into the passage 26 in the tube fitting 20, through the channel 36 and out the outlet 39 of the channel section 30, preferably towards the inlet 118 of the speaking valve 110. In addition, the gripping flanges 40 preferably engage the outer wall 112 of the speaking valve 110 such that the adapter 10 may pivot peripherally around the speaking valve 110 to facilitate aligning the tube fitting 20 with the oxygen tubing (not shown).

An important feature of the adapter 10 of the present invention is the delivery of oxygen at the inlet 118 of the speaking valve 110. When a patient using the adapter 10 inhales, oxygen being delivered to the inlet 116 may freely enter into the speaking valve 110 past the open diaphragm 120. When the patient exhales, the diaphragm 120 closes, preventing oxygen from entering the tracheostomy tube 100. Oxygen is delivered under conditions more closely simulating natural breathing, rather than subjecting the patient to constant positive pressure from the oxygen source which may cause pneumothorax and/or contribute to other adverse side effects, such as dryness in the throat.

In addition, an important safety feature of the present invention is the semi-rigid nature of the gripping flanges. If tubing attached to the adapter is accidentally snagged and pulled, the gripping flanges may disengage the outer wall of the speaking valve, allowing the adapter to be pulled off of the speaking valve. This substantially minimizes subjecting the speaking valve and/or the tracheostomy tube to unexpected forces that may cause distress to the patient and/or damage the tracheostomy tube.

Furthermore, the adapter maintains the low profile generally desired to protect the patient and the tracheostomy tube. With the adapter of the present invention, the oxygen tubing connected to the speaking valve is located close to the hub on the tracheostomy tube, rather than extending axially from the inlet end of the speaking valve. This substantially minimizes stresses on the tube and consequently on the patient.

Those skilled in the art will appreciate that the embodiment described above is only exemplary of an adapter and speaking valve in accordance with the present invention. For example, in an alternative embodiment, an oxygen adapter similar to that described may be provided integral with a speaking valve, for example from a single-piece of injection-molded plastic. A tube fitting may be formed extending from an outer wall of the speaking valve, preferably projecting radially therefrom. A channel may be formed directly in the outer wall communicating between the tube fitting and an inlet end of the speaking valve, preferably by a plurality of channel walls molded directly into the outer wall. An outlet end of the channel may include a cowling extending around the inlet end adapted to direct oxygen passing through the channel towards the diaphragm. Thus, the advantages of oxygen delivery to the inlet of the diaphragm and the relatively low profile of the device is achieved, although a cap may be required to close the tube fitting when not in use to deliver oxygen.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An adapter for detachably connecting tubing to a tracheostomy speaking valve having an outer wall and an inlet end, said adapter comprising:
    means for connecting the adapter to the outer wall of the speaking valve;
    a tube fitting adapted to receive tubing thereon, said tube fitting having a passage therein adapted to communicate with tubing received thereon, said tube fitting extending from the outer wall of the speaking valve when said adapter is connected to the speaking valve; and
    a channel section attached to and extending from said tube fitting, said channel section comprising a plurality of walls defining a channel communicating between said passage and an outlet end of said channel section, said outlet end being adapted to be located adjacent the inlet end of the speaking valve when said adapter is connected to the speaking valve.

2. The adapter of claim 1, wherein said channel section extends substantially perpendicularly from said tube fitting.

3. The adapter of claim 1, wherein said channel section extends axially along the outer wall of the speaking valve between said tube fitting and the inlet end of the speaking valve when said adapter is connected to the speaking valve.

4. The adapter of claim 3, wherein said plurality of walls substantially follow the contour of the outer wall of the speaking valve, said channel thereby maintaining a substantially uniform cross-section.

5. The adapter of claim 3, wherein said outlet end of said channel section partially covers an inlet in the inlet end of the speaking valve, thereby defining a cowling adapted to deliver oxygen from tubing attached to said tube fitting to the inlet of the speaking valve.

6. The adapter of claim 1, wherein said plurality of walls of said channel section comprises a top wall and two side walls.

7. The adapter of claim 6, wherein said side walls substantially engage the outer wall of the speaking valve when said adapter is connected to the speaking valve, the outer wall thereby further defining said channel.

8. The adapter of claim 1, wherein said plurality of walls comprise a top wall, two side walls, and a bottom wall defining said channel.

9. The adapter of claim 1, wherein said means for connecting said tube fitting to the speaking valve comprises gripping members attached to said tube fitting, said gripping members being adapted to peripherally engage the outer wall of the speaking valve.

10. The adapter of claim 9, wherein said gripping members comprise curved gripping flanges, said gripping flanges substantially defining at least half of an annulus, said gripping flanges having an inner surface partially defining a substantially cylindrical shape similar to the outer wall of the speaking valve.

11. The adapter of claim 10, wherein said gripping flanges comprise a semi-rigid material, thereby allowing said gripping flanges to resiliently open to detachably connect said adapter to the speaking valve.

12. The adapter of claim 1, where said tube fitting extends substantially radially from the outer wall when said adapter is connected to the speaking valve.

13. The adapter of claim 1, wherein said adapter comprises injection-molded plastic.

14. An adapter for detachably connecting tubing to a tracheostomy speaking valve having an outer wall and an inlet end, said adapter comprising:
    a gripping member adapted to connect said adapter to the outer wall of the speaking valve;
    a tube fitting adapted to receive tubing thereon, said tube fitting having a passage therein adapted to communicate with tubing received thereon, said tube fitting extending substantially radially from the outer wall of the speaking valve when said adapter is connected to the speaking valve; and
    a channel section attached to and extending substantially perpendicularly from said tube fitting, said channel section comprising a plurality of walls defining a channel communicating between said passage and an outlet end of said channel section, said outlet end being adapted to be located adjacent the inlet end of the speaking valve when said adapter is connected to the speaking valve.

15. An adapter for delivering supplemental oxygen to a tracheostomized patient using a speaking valve, the speaking valve having a cylindrical outer wall and an inlet end, said adapter comprising:
    a port having a base and an outer end, and having a passage extending between said base and said outer end, said outer end being attachable to a source of supplemental oxygen, said port extending substantially radially from the cylindrical outer wall of the speaking valve when said adapter is connected to the speaking valve;
    a pair of semi-rigid gripping flanges attached to said base of said port, and being adapted to peripherally engage the cylindrical outer wall of the speaking valve, thereby detachably connecting said adapter to the speaking valve; and
    an outlet section attached to said port, said outlet section including a plurality of walls defining a channel, said channel communicating between said passage and an outlet end of said outlet section, said outlet end being located adjacent the inlet end of the speaking valve when said adapter is connected to the speaking valve, thereby delivering oxygen from the source attached to said port to the inlet end of the speaking valve.

16. The adapter of claim 15, wherein said outlet section substantially abuts and extends axially along the cylindrical outer wall when said adapter is connected to the speaking valve.

17. The adapter of claim 15, wherein said plurality of walls comprise a top wall and two side walls, said side walls substantially engaging the outer wall of the speaking valve, the outer wall defining a bottom wall of said channel, thereby allowing oxygen to travel through said channel.

18. The adapter of claim 15, wherein said port comprises a tube fitting adapted to receive tubing for delivering supplemental oxygen on said outer end.

19. The adapter of claim 18, wherein said tube fitting is pivotally attached to said base.

20. The adapter of claim 15, wherein said adapter comprises injection-molded plastic.

21. The adapter of claim 15, wherein said port, said gripping flanges, and said outlet section are integrally molded together.

22. An adapter for delivering supplemental oxygen to a tracheostomized patient using a speaking valve, the speaking valve having a cylindrical outer wall and an inlet end, said adapter comprising:
   a port having a base and an outer end, and having a passage extending between said base and said outer end, said outer end being attachable to a source of supplemental oxygen, said port extending substantially radially from the cylindrical outer wall of the speaking valve when said adapter is connected to the speaking valve;
   a pair of semi-rigid gripping flanges extending from said base of said port, and being adapted to peripherally engage the cylindrical outer wall of the speaking valve, thereby detachably connecting said adapter to the speaking valve; and
   an outlet section extending from said port, said outlet section including a plurality of walls defining a channel, said channel communicating between said passage and an outlet end of said outlet section, said outlet end being located adjacent the inlet end of the speaking valve when said adapter is connected to the speaking valve, thereby delivering oxygen from the source attached to said port to the inlet end of the speaking valve.

23. A device for delivering supplemental oxygen into a tracheostomy tube in a patient, said device comprising:
   a speaking valve having a substantially cylindrical wall, an inlet end and an outlet end, said inlet end having a check valve therein allowing air flow into the speaking valve, said outlet end being attachable to the tracheostomy tube;
   an oxygen adapter attached to said speaking valve, said adapter including a tube fitting and an outlet section, said tube fitting extending from said cylindrical wall of said speaking valve, and being adapted to receive supplemental oxygen tubing thereon, said outlet section defining a channel extending from said tube fitting to said inlet end of said speaking valve, thereby delivering oxygen from tubing connected to said tube fitting through said channel to said inlet end of said speaking valve.

24. The device of claim 23, wherein said oxygen adapter includes semi-rigid gripping flanges adapted to detachably connect said adapter to said speaking valve.

25. The device of claim 23, wherein said outlet section comprises side walls substantially engaging said cylindrical wall of said speaking valve, said cylindrical wall thereby partially defining said channel.

26. The device of claim 23, wherein said outlet section comprises a top wall, said top wall substantially following the contour of said cylindrical wall, thereby maintaining a substantially uniform cross-section for said channel.

27. The device of claim 23, wherein said tube fitting extends radially from said cylindrical wall of said speaking valve.

28. A speaking valve capable of delivering supplemental oxygen into a tracheostomy tube in a patient, said speaking valve comprising:
   a cylindrical body having a substantially cylindrical wall, an inlet end and an outlet end, said inlet end having a check valve therein allowing air flow into said cylindrical body, said outlet end being attachable to a tracheostomy tube;
   a tube fitting extending from said cylindrical wall and being adapted to receive supplemental oxygen tubing thereon; and
   a plurality of walls extending along said cylindrical wall between said tube fitting and said inlet end of said cylindrical body, said plurality of walls defining a channel communicating between said tube fitting and said inlet end of said cylindrical body, thereby delivering oxygen from tubing connected to said tube fitting through said channel to said inlet end.

* * * * *

UNITED STATES PATENT AND TRADEMARK OFFICE
CERTIFICATE OF CORRECTION

PATENT NO. : 5,806,515
DATED : September 15, 1998
INVENTOR(S) : Rex O. Bare, et al.

It is certified that error appears in the above-identified patent and that said Letters Patent is hereby corrected as shown below:

Column 1, line 67, change "possible" to -- possibly --.

Column 6, line 13, change "42" to -- 40 --.

Signed and Sealed this

Fourteenth Day of March, 2000

Attest:

Q. TODD DICKINSON

*Attesting Officer*    *Commissioner of Patents and Trademarks*